US011141230B2

(12) United States Patent
Zhou et al.

(10) Patent No.: US 11,141,230 B2
(45) Date of Patent: *Oct. 12, 2021

(54) ACTIVE BACKDRIVING FOR A ROBOTIC ARM

(71) Applicant: Verb Surgical Inc., Santa Clara, CA (US)

(72) Inventors: Renbin Zhou, Wellington, FL (US); Sina Nia Kosari, Fremont, CA (US); Dennis Moses, Hollywood, FL (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/034,703

(22) Filed: Sep. 28, 2020

(65) Prior Publication Data

US 2021/0007812 A1 Jan. 14, 2021

Related U.S. Application Data

(63) Continuation of application No. 15/838,094, filed on Dec. 11, 2017, now Pat. No. 10,786,317.

(51) Int. Cl.
*A61B 34/30* (2016.01)
*A61B 34/37* (2016.01)
(Continued)

(52) U.S. Cl.
CPC ........ *A61B 34/30* (2016.02); *A61B 17/00234* (2013.01); *A61B 34/10* (2016.02);
(Continued)

(58) Field of Classification Search
CPC ......... A61B 34/30; A61B 34/70; A61B 34/10; A61B 34/37; A61B 17/00234; A61B 34/20
(Continued)

(56) References Cited

U.S. PATENT DOCUMENTS 5,382,885 A 1/1995 Salcudean et al.
6,451,027 B1 9/2002 Cooper et al.
(Continued)

FOREIGN PATENT DOCUMENTS

EP 2602676 3/2013
EP 2602676 6/2013
(Continued)

OTHER PUBLICATIONS

Examination Report for Australian Application No. 2017443223 dated Aug. 21, 2020, 4 pages.
(Continued)

*Primary Examiner* — Jaime Figueroa
(74) *Attorney, Agent, or Firm* — Womble Bond Dickinson (US) LLP (57) ABSTRACT

A robotic surgical system includes at least one robotic arm comprising at least one movable joint and an actuator configured to drive the at least one movable joint, and a controller configured to generate a first signal, the first signal comprising a first oscillating waveform having a first frequency and being modulated by a second oscillating waveform having a second frequency, wherein the second frequency is higher than the first frequency. The actuator is configured to drive the at least one movable joint based on the first signal to at least partially compensate for friction in the at least one movable joint.

19 Claims, 9 Drawing Sheets

(51) Int. Cl.
*A61B 34/00* (2016.01)
*A61B 34/10* (2016.01)
*A61B 17/00* (2006.01)
*A61B 34/20* (2016.01)

(52) U.S. Cl.
CPC .............. *A61B 34/37* (2016.02); *A61B 34/70* (2016.02); *A61B 34/20* (2016.02)

(58) Field of Classification Search
USPC ........................................................ 700/245
See application file for complete search history.

(56) References Cited

U.S. PATENT DOCUMENTS

| | | | |
|---|---|---|---|
| 6,723,106 | B1 | 4/2004 | Charles et al. |
| 6,786,896 | B1 | 9/2004 | Madhani et al. |
| 7,843,158 | B2 | 11/2010 | Prisco |
| 8,004,229 | B2 | 8/2011 | Nowlin et al. |
| 8,864,751 | B2 | 10/2014 | Prisco et al. |
| 9,221,172 | B2 | 12/2015 | Williamson et al. |
| 10,661,453 | B2 * | 5/2020 | Koenig .................. A61B 34/70 |
| 10,828,115 | B2 * | 11/2020 | Koenig ................ B25J 17/0283 |
| 10,828,769 | B2 * | 11/2020 | Meissner ............... B25J 9/1656 |
| 2005/0183532 | A1 | 8/2005 | Najafi et al. |
| 2006/0041249 | A1 | 2/2006 | Niemeyer |
| 2008/0161829 | A1 | 7/2008 | Kang |
| 2008/0238391 | A1 | 10/2008 | Williams et al. |
| 2009/0005913 | A1 | 1/2009 | Fernandez et al. |
| 2009/0248038 | A1 | 10/2009 | Blumenkranz et al. |
| 2011/0282491 | A1 | 11/2011 | Prisco et al. |
| 2012/0123395 | A1 | 5/2012 | Stoy et al. |
| 2013/0131649 | A1 | 5/2013 | Hughett, Sr. et al. |
| 2014/0005667 | A1 | 1/2014 | Stulen et al. |
| 2014/0039517 | A1 | 2/2014 | Bowling et al. |
| 2014/0039681 | A1 | 2/2014 | Bowling et al. |
| 2014/0188129 | A1 | 7/2014 | Kang |
| 2014/0222207 | A1 | 8/2014 | Bowling et al. |
| 2014/0276952 | A1 | 9/2014 | Hourtash et al. |
| 2014/0343567 | A1 | 11/2014 | Morash |
| 2015/0133961 | A1 | 5/2015 | Uchida et al. |
| 2015/0374446 | A1 | 12/2015 | Malackowski et al. |
| 2017/0027655 | A1 | 2/2017 | Niemeyer |
| 2017/0128136 | A1 | 5/2017 | Post |
| 2017/0245955 | A1 | 8/2017 | Bowling et al. |
| 2018/0014897 | A1 | 1/2018 | Peine |
| 2019/0216555 | A1 | 7/2019 | DiMaio et al. |

FOREIGN PATENT DOCUMENTS

| | | |
|---|---|---|
| EP | 2980986 | 2/2016 |
| JP | 2004344998 | 12/2004 |
| JP | 2017-78498 | 4/2017 |
| WO | 2010090059 | 8/2010 |
| WO | 2017014216 | 1/2017 |

OTHER PUBLICATIONS

Outgoing Written Opinion of the ISA, dated Feb. 14, 2018 for International Application No. PCT/US2017/065636.
Outgoing—ISA/210—International Search Report, dated Feb. 14, 2018 for International Application No. PCT/US2017/065636.
ISA/220—Notification of Transmittal or Search Report and Written Opinion of the ISA, or the Declaration dated Feb. 14, 2018 for International Application No. PCT/US2017/065636.
International Preliminary Report on Patentabilitiy for International Application No. PCT/US2017/065636 dated Jun. 25, 2020, 8 pages.
Extended European Search Report for European Application No. 17934358.7 dated Aug. 11, 2020, 38 pages.
Examiner's Report for Canadian Application No. 3,079,347 dated May 18, 2021, 3 pages.
Notification of Reasons for Refusal for Japanese Application No. 2020-525972 dated Jun. 29, 2021, 8 pages.

* cited by examiner

ACTIVE BACKDRIVING FOR A ROBOTIC ARM

This application is a continuation of pending U.S. application Ser. No. 15/838,094 filed Dec. 11, 2017.

TECHNICAL FIELD

This invention relates generally to the field of robotic surgery, and more specifically to new and useful systems and methods for assisting backdriving of a robotic arm.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical instruments (e.g., end effector, at least one camera, etc.) through the incisions into the patient. The surgical procedures may then be performed using the introduced surgical instruments, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator. A robotic arm may, for example, support at its distal end various devices such as surgical end effectors, imaging devices, cannulae for providing access to the patient's body cavity and organs, etc. The robotic arm and surgical instruments may be controlled to perform minimally-invasive surgery.

Typically, a robotic arm in a robotic surgical system includes one or more joints enabling movement of the robotic arm. For example, at least one joint may be driven by an actuator assembly including a motor, a gear train, one or more sensors, etc. The actuator assembly may furthermore be backdriven, such as due to a user exerting a manual force on the robotic arm to reposition the joint and/or other joints of the robotic arm. However, due to factors such as high gear ratios in gear trains and/or high friction between interfacing mechanical components, the one or more joints in the robotic arm may experience high friction when being backdriven, thereby requiring a greater force to overcome the high friction and backdrive the actuator assemblies. This may, for example, make it difficult for a user to manually reposition the arm. Thus, it is desirable to have systems and methods for assisting backdriving of a robotic arm.

SUMMARY

Generally, in some variations, a method for assisting movement of a robotic surgical arm having at least one movable joint may include generating a modulated signal comprising a first oscillating waveform having a first frequency and being modulated by a second oscillating waveform having a second frequency, and driving an actuator in the at least one movable joint based on the modulated signal to at least partially compensate for friction in the at least one movable joint. The second frequency may be higher than the first frequency. Furthermore, the method may include detecting movement of the at least one movable joint, generating a second signal different from the modulated signal, and driving the actuator in the at least one movable joint based on the second signal to at least partially compensate for friction in the joint.

Furthermore, generally, in some variations, a robotic surgical system may include at least one robotic arm comprising at least one movable joint and an actuator configured to drive the at least one movable joint, and a controller configured to generate a modulated signal, wherein the actuator is configured to drive the at least one movable joint based on the modulated signal to at least partially compensate for friction in the at least one movable joint. The modulated signal may include a first oscillating waveform having a first frequency and being modulated by a second oscillating waveform having a second frequency, where the second frequency is higher than the first frequency. In some variations, the system may include at least one sensor configured to detect movement of the at least one movable joint. Upon detection of joint movement, the control system may be configured to generate a second signal different from the modulated signal, and the actuator may be configured to drive the at least one movable joint based on the second signal to at least partially compensate for friction in the joint.

The first and/or second oscillating waveforms for the modulated signal may be, for example, a sine wave. In some variations, the first frequency of the first oscillating waveform may be between about 1 Hz and about 5 Hz (e.g., about 2 Hz). The second frequency of the second oscillating waveform may be less than or equal to about 200 Hz (e.g., about 100 Hz). The first and/or second signals may be based on a dynamic friction model (e.g., Couloumb friction model, viscous friction model), such that, for example, the second signal may be generally proportional to the velocity of the at least one movable joint to continue to at least partially compensate for friction in the joint.

In some variations, the actuator may also be driven to at least partially compensate for a gravitational force acting upon the at least one movable joint. In these variations, friction compensation and gravity compensation may be concurrently performed to assist a user manipulating the arm with ease (e.g., a user desiring to manually manipulate the robotic arm, leave the robotic arm temporarily, and continue manually manipulating the robotic arm and without complications caused by gravity and/or friction within the robotic arm.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

Robotic Surgical System Overview

Figure 1A:
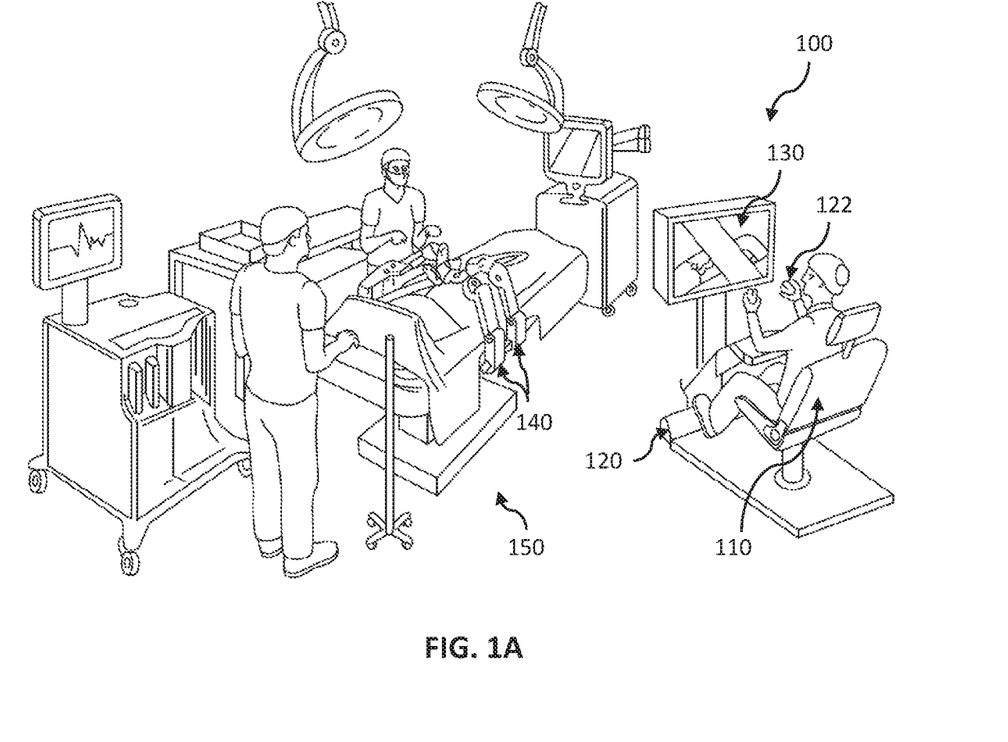
FIG. 1A depicts an example of an operating room arrangement with a robotic surgical system and a surgeon console.
Figure 1B:
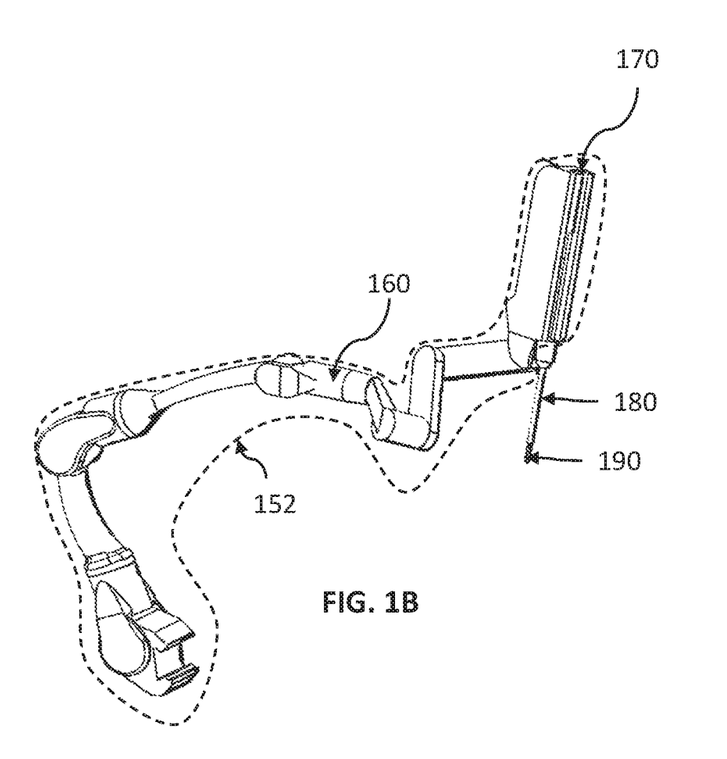
FIG. 1B is a schematic illustration of one exemplary variation of an instrument driver on a robotic arm.

Generally, as shown in FIG. 1A, a robotic system 150 may include one or more robotic arms 160 located at a surgical platform (e.g., table, bed, cart, etc.), where end effectors or surgical tools are attached to the distal ends of the robotic arms 160 for executing a surgical procedure. For example, a robotic system 150 may include, as shown in the exemplary schematic of FIG. 1B, at least one robotic arm 160 coupled to a surgical platform, and an instrument driver 170 generally attached to a distal end of the robotic arm 160. A cannula 180 coupled to the end of the instrument driver 170 may receive and guide a surgical instrument 190 (e.g., end effector, camera, etc.). Furthermore, the robotic arm 160 may include a plurality of links that are actuated so as to position and orient the instrument driver 170, which actuates the surgical instrument 190. A sterile drape 152 or other sterile barrier may be interposed between non-sterile components (e.g., robotic arm 160 and instrument driver 170) and sterile components (e.g., cannula 180) to help maintain a sterile field for the patient (e.g., to protect against contamination from non-sterile components).

A user (such as a surgeon or other operator) may use a user console 100 to remotely manipulate the robotic arms 160 and/or surgical instruments (e.g., tele-operation). The user console 100 may be located in the same procedure room as the robotic system 150, as shown in FIG. 1A. In other embodiments, the user console 100 may be located in an adjacent or nearby room, or tele-operated from a remote location in a different building, city, or country, etc.

In one example, the user console 100 comprises a seat 110, foot-operated controls 120, one or more handheld user interface devices 122, and at least one user display 130 configured to display, for example, a view of the surgical site inside a patient. For example, a user located in the seat 110 and viewing the user display 130 may manipulate the foot-operated controls 120 and/or handheld user interface devices 122 to remotely control the robotic arms 160 and/or surgical instruments.

During an exemplary procedure or surgery, the patient is prepped and draped in a sterile fashion, and anesthesia is achieved. Initial access to the surgical site may be performed (e.g., with an incision in the patient). Once access is completed, initial positioning and/or preparation of the robotic system may be performed. During the surgical procedure, a surgeon or other user in the user console 100 may utilize the foot-operated controls 120 and/or user interface devices 122 to manipulate various end effectors and/or imaging systems to perform the procedure. Manual assistance may also be provided at the procedure table by sterile-gowned personnel, who may perform tasks including but not limited to retracting organs, or performing manual repositioning or tool exchange involving one or more robotic arms 160. Non-sterile personnel may also be present to assist the surgeon at the user console 100. When the procedure or surgery is completed, the robotic system 150 and/or user console 100 may be configured or set in a state to facilitate one or more post-operative procedures, including but not limited to robotic system 150 cleaning and/or sterilization, and/or healthcare record entry or printout, whether electronic or hard copy, such as via the user console 100.

In FIG. 1A, the robotic arms 160 are shown with a table-mounted system, but in other embodiments, the robotic arms may be mounted in a cart, ceiling or sidewall, or other suitable support surface. The communication between the robotic system 150, the user console 100, and any other displays may be via wired and/or wireless connection(s). Any wired connections may be optionally built into the floor and/or walls or ceiling. The communication between the user console 100 and the robotic system 150 may be wired and/or wireless, and may be proprietary and/or performed using any of a variety of data communication protocols. In still other variations, the user console 100 does not include an integrated display 130, but may provide a video output that can be connected to output to one or more generic displays, including remote displays accessible via the internet or network. The video output or feed may also be encrypted to ensure privacy and all or portions of the video output may be saved to a server or electronic healthcare record system.

In other examples, additional user consoles 100 may be provided, for example to control additional surgical instruments, and/or to take control of one or more surgical instruments at a primary user console. This will permit, for example, a surgeon to take over or illustrate a technique during a surgical procedure with medical students and physicians-in-training, or to assist during complex surgeries requiring multiple surgeons acting simultaneously or in a coordinated manner.

Robotic Arm

Figure 2A:
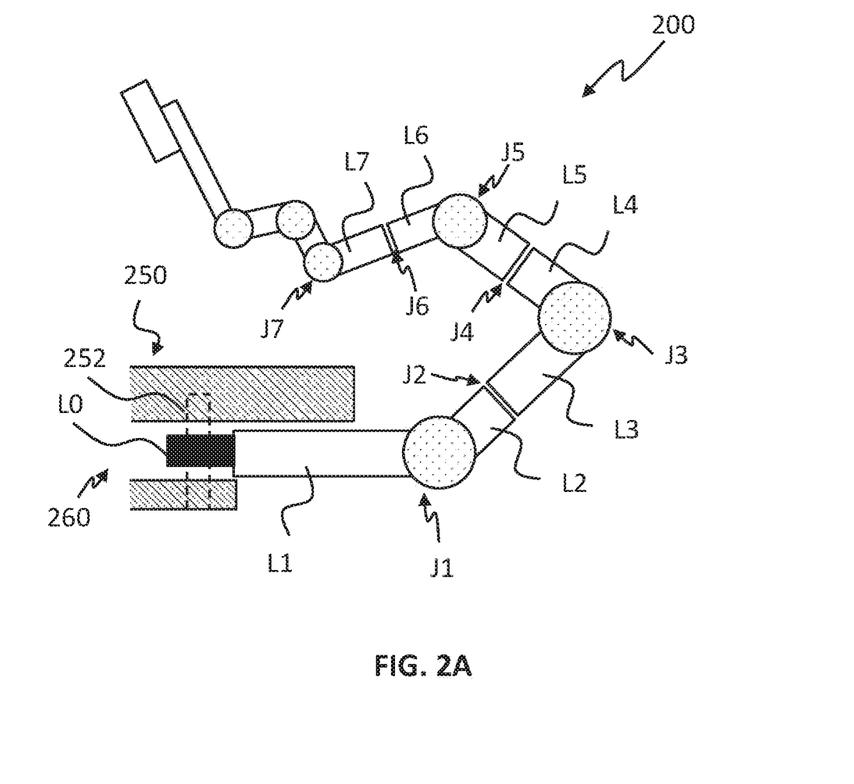
FIG. 2A is a schematic illustration of another exemplary variation of an instrument driver on a robotic arm, coupled to a patient table.

Generally, as described above, one or more robotic arms in a robotic surgical system may be located at a surgical platform, such as a table, bed, cart, etc. For example, as shown in FIG. 2A, one exemplary variation of a robotic arm 200 may be coupled to a table 250 via a coupling arrangement 260. The coupling arrangement 260 may enable the robotic arm 200 to pivot or move laterally relative to the surface of the table 250 (in and out of the page, as shown in the orientation of FIG. 2A). The coupling arrangement 260 may, for example, include a pin 252 coupled to the table 250, and a coupling link L0 rotatably coupled to the pin 252 so as to form a pivot joint or pin joint. The coupling arrangement 260 may further include an actuator (e.g., motor and gear train) configured to enable powered movement of the robotic arm 200 relative to the table 250 via an actuatable joint around pin 252. The coupling arrangement 260 may include at least one position sensor, such as an encoder coupled to an actuator in the coupling arrangement 260 or another suitable angle sensor, configured to measure the position or orientation of the robotic arm 200 relative to the table 250. Furthermore, in some variations, one or more brakes may be included in the coupling arrangement 260 so as to selectively arrest relative movement of the robotic arm 200 relative to the table 250.

Although the robotic arm 200 is primarily described herein as being coupled to the table 250 via a pivotable coupling arrangement, it should be understood that in other variations, the robotic arm 200 may additionally or alternatively be coupled to the patient table with other kinds of mechanisms, including but not limited to mechanisms facilitating longitudinal or lateral movement, such as tracks, pin-in-slot, or other suitable mechanisms. Furthermore, the methods described herein may be used to assist backdriving in other variations of robotic arms (e.g., different structures, different coupling arrangements to a surface, etc.).

The robotic arm 200 may include multiple links (arm segments), and a multiple actuated joint modules that drive or regulate relative movement between adjacent links. Each joint module may include an actuator, a gear train (e.g., harmonic drive), encoder, torque sensor, force sensor, and/or other suitable actuator, transmission, etc. for moving arm links, and/or suitable sensors for detecting positional and/or torque feedback. Such feedback may, for example, be used to provide input into control schemes operating the robotic arm. One or more joint modules may include one or more brakes (e.g., drum brake) that may arrest relative movement of adjacent links and/or hold or lock relative positions of adjacent links, such as for holding the robotic arm in a particular pose or configuration.

As shown in FIG. 2A, one exemplary variation of a robotic arm 200 may include at least seven joint modules actuating joints J1-J7 in the robotic arm 200, where J1-J7 includes pivot joints and/or roll joints. J1 may enable relative pivot movement between a first link L1 and a second link L2. J2 may enable relative roll movement between the second link L2 and a third link L3. J3 may enable relative pivot movement between the third link L3 and a fourth link L4. J4 may enable relative roll movement between the fourth link L4 and a fifth link L5. J5 may enable relative pivot movement between the fifth link L5 and a sixth link L6. J6 may enable relative roll movement between the sixth link L6 and a seventh link L7. J7 may enable relative pivot movement between the seventh link L7 and an eighth link L8. For example, in some variations, the combination of pivot joints J1, J3, J5, and J7 and roll joints J2, J4, and J6 may enable a robotic arm that has at least seven degrees of freedom and is movable into various configurations including those described herein. However, it should be understood that the robotic arm shown in FIG. 2 is exemplary only, and the methods described herein may be used to control any suitable kind of robotic arm. Other exemplary variations of a robotic arm are described in U.S. patent application Ser. No. 15/706,536 entitled "ROBOTIC ARMS" and filed Sep. 15, 2017, which is incorporated herein in its entirety by this reference.

Control System

Figure 2B:
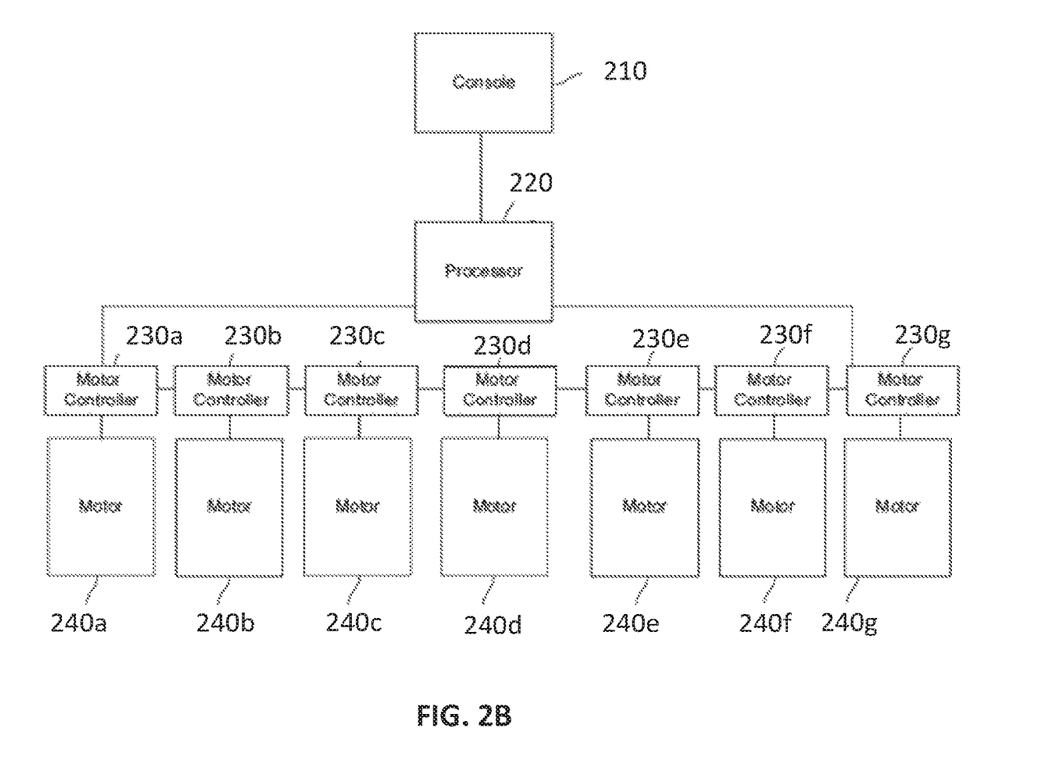
FIG. 2B is an overview schematic of an exemplary control system setup for controlling actuation of the joint modules of one exemplary variation of a robotic arm.

In some variations, the robotic arm may be generally controlled by a control system that governs actions of the robotic arm. The control system may control multiple robotic arms, if the robotic-assisted surgical system includes more than one robotic arm. For example, as shown in FIG. 2B, the control system may include one or more processors 220 (e.g., a microprocessor, microcontroller, application-specific integrated circuit, field programmable gate array, and/or other logic circuitry). The processor 220, which may be located on the robotic arm itself, in a cart-carried unit, or other suitable structure, may be communicatively linked to a console 210 (e.g., a user interface). The processor 220 may be configured to execute instructions for performing any combination of aspects of the methods, and/or combinations of the methods described herein. The control system may further include a set of one or more motor controllers (e.g., 230a-230g), each of which is communicatively coupled to the processor 220 and dedicated to control and operate at least one actuator in a respective joint module in the robotic arm (e.g., 240a-240g).

In some variations, the control system may be configured to generate at least one modulated signal for controlling movement of a joint module in a robotic arm. For example, at least one actuator in the robotic arm may be configured to drive (e.g., apply a first load on) a respective movable joint in accordance with the modulated signal to at least partially compensate for friction in the movable joint. The modulated signal may include a first oscillating waveform having a first frequency and being modulated by a second oscillating waveform having a second frequency, wherein the second frequency is higher than the first frequency. In some variations, the first frequency of the first oscillating waveform may be at least partially based on a desired promptness of response to detection of an external force (e.g., user-applied force) on the movable joint in the robotic arm. The second oscillating waveform, which may have an amplitude to increase the magnitude of the modulated signal to a suitable level (e.g., for helping the external force overcome friction), may have a second frequency that is selected at least in part to avoid generating audible humming. For example, the first oscillating waveform may have a frequency of between about 1 Hz and about 5 Hz, and the second oscillating waveform may have a frequency of less than or equal to about 200 Hz. In variations in which the first oscillating waveform has a frequency of about 2 Hz, for example, there are about two times per second when the modulated signal is both at its maximum magnitude and drives a joint module actuator in the same direction in which a user is pushing on a joint. Therefore, there are generally about two times per second when the modulated signal is most likely to successfully assist the user in moving the joint. Furthermore, as described further herein, the control system may additionally or alternatively generate a signal with which at least one actuator is configured to drive (e.g., apply a second load on) a respective movable joint to at least partially compensate for a gravitational force acting upon the moveable joint.

Figure 3:
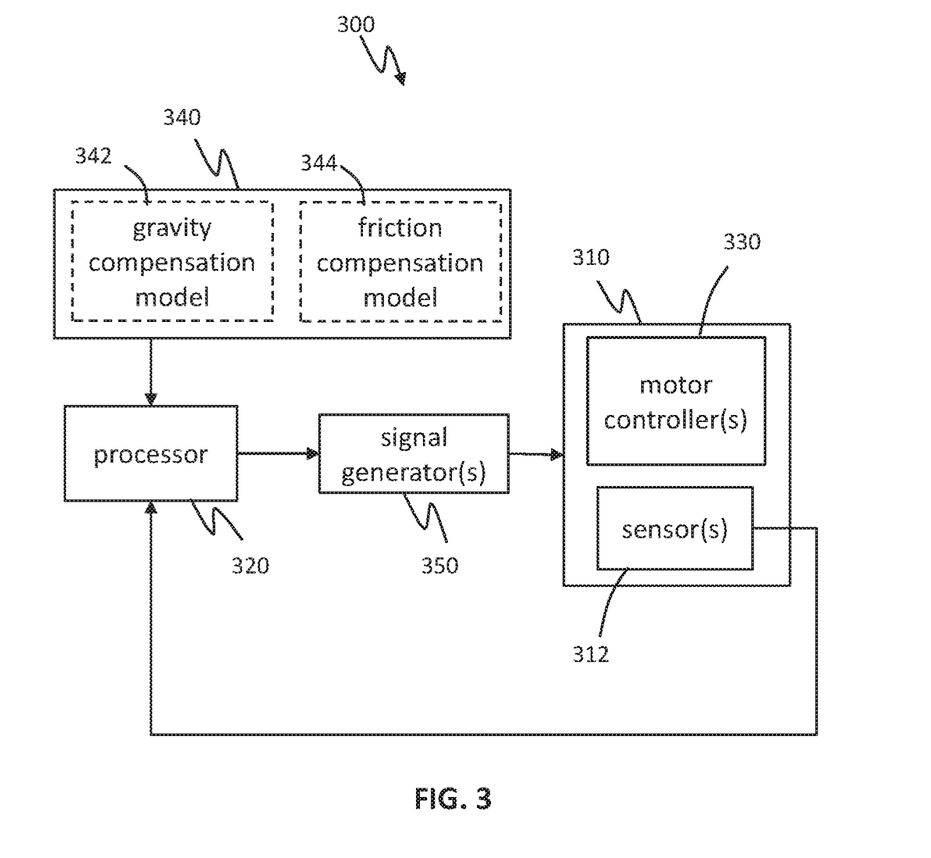
FIG. 3 is a schematic illustration of an exemplary variation of a control system for assisting movement (e.g., backdriving) of a robotic arm.

For example, FIG. 3 is a schematic illustration of another variation of a control system 300 for a robotic arm 310. The control system 300 may include at least one processor 320 configured to execute instructions for generating motor command signals via one or more signal generators 350, where the motor command signals may be used by one or more motor controllers 330 to drive one or more respective joints in the robotic arm 310. The processor 320 and signal generator(s) 350 may, for example, be configured to generate motor command signals based on a gravity compensation model 342 and/or a friction compensation model 344 stored in (and received from) memory 340, as further described below. The memory 340 may, for example, be local or remote storage media (e.g., RAMs, ROMs, flash memory, EEPROMs, optical devices such as CD or DVD, hard drives, floppy drives, etc.). Furthermore, control system inputs for the gravity compensation model 342 and/or friction compensation model 344 may be provided by one or more sensors 312 in the robotic arm (e.g., encoder, torque sensor, force sensor, accelerometer, etc. in at least one joint module or other suitable portion of the robotic arm 310), as described in further detail below.

Gravity Compensation

In a gravity compensation control mode, the control system commands one or more actuators in the robotic arm such that the robotic arm holds itself in a particular pose without drifting downward due to gravity. In gravity compensation mode, the control system determines the gravity force acting on at least a portion of the links in the robotic arm (e.g., based on a gravity compensation model 342). In response, the control system actuates at least one joint module to counteract the determined gravity force such that the robotic arm can maintain the current pose. To determine the gravity force, for example, the control system may perform calculations based on measured joint angles between adjacent links, known kinematic and/or dynamic properties of the robotic arm and instrument driver, and/or known characteristics of the actuator (e.g., gear ratio, motor torque constants), detected force(s) on joints, etc. Furthermore, the robotic arm may include at least one accelerometer or other suitable sensor(s) configured to determine the direction of the applied gravitational force on the arm.

Based on these calculations, the control system may algorithmically determine what force at each joint module is needed to compensate for gravity force acting on that joint module. For example, the controller may utilize a forward kinematic algorithm, an inverse dynamic algorithm, or any suitable algorithm (e.g., in accordance with a gravity compensation model 342). The control system may then generate a set of commands to provide the actuators in the joint modules with an appropriate level of current which holds the robotic arm in the same pose. The gravity compensation mode may be used alone or in combination with other control modes (e.g., friction compensation mode described below).

Friction Compensation

Figure 4:
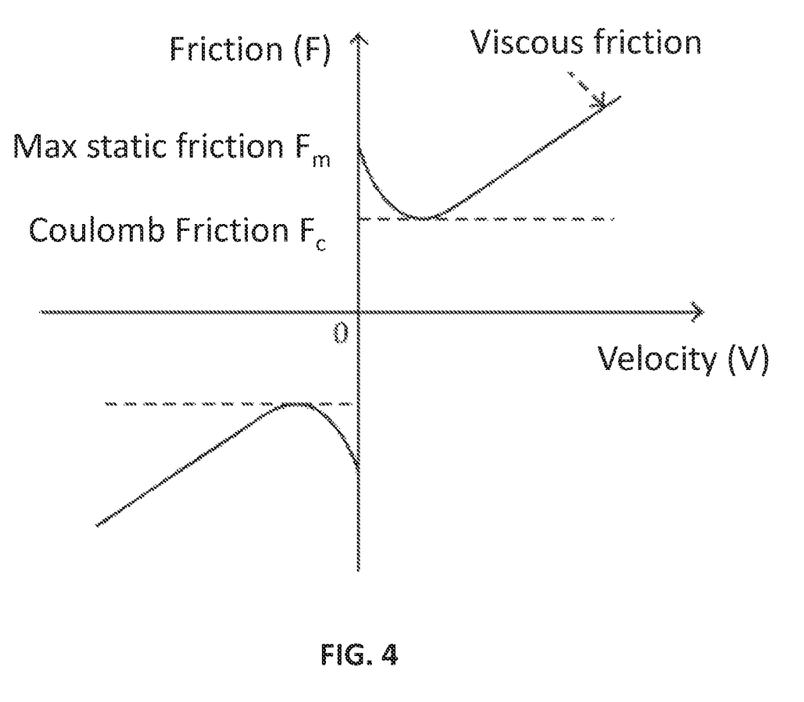
FIG. 4 illustrates an exemplary friction model describing frictional force F as a function of relative velocity V of a moving object in contact with another object.

FIG. 4 illustrates an exemplary friction model describing frictional force F as a function of relative velocity V of a moving object in contact with another object. More specifically, FIG. 4 depicts a friction model including Coulomb friction and linear viscous friction, with Stribeck effect. In some situations, when velocity is zero, the starting static friction force $F_m$ is higher than the friction force occurring immediately after relative movement commences. After sliding begins and while velocity V is within a certain velocity regime, friction decreases with increasing velocity in what is termed the Stribeck effect. Coulomb friction force $F_c$, which corresponds to the minimum of the curve describing the Stribeck effect, originates from the shear resistance between the contacting portions of the two objects. As relative velocity of the moving object increases from the minimum of the Stribeck curve, a viscous friction force is generally linear with respect to the velocity V. Both a positive region (corresponding to velocity in a first direction) and a negative region (corresponding to velocity in a second direction opposite to the first direction) of the friction model are depicted in the schematic of FIG. 4. In order to move one component relative to another component that is in contact with the moving component, an external force must be applied to the moving component such that the external force generally exceeds the frictional force as summarized in the schematic of FIG. 4.

In the context of the systems and methods described herein, in some variations, the robotic arm may be operated in a friction compensation mode, or active backdrive mode, that helps to generate enough force to overcome frictional force resisting movement of the robotic arm. For example, in some situations, a user may wish to directly or manually manipulate (e.g., pull or push) one or more of the arm links to arrange the robotic arm in a particular pose. These actions backdrive the actuators of the robotic arm. However, due to friction caused by mechanical aspects such as high gear ratios in the joint modules, in some variations, the user must apply a significant amount of force in order to overcome the friction and successfully move the robotic arm. To address this, the friction compensation mode enables the robotic arm to assist a user in moving at least a portion of the robotic arm, by determining the presence and direction of a user-applied force acting on at least one joint module (either directly or indirectly as the result of force on one or more arm links) to backdrive the actuator in that joint module, and then actively driving appropriate joint modules in the direction needed to achieve the pose desired by the user. In other words, the control system for the robotic arm may actuate one or more joint modules in the same direction as the user-applied force to help the user overcome static or dynamic friction. As a result, the user may manually manipulate the robotic arm with less perceived friction. The friction compensation mode may, in some variations, be used alone or in combination with other modes (e.g., gravity compensation mode).

Figure 5:
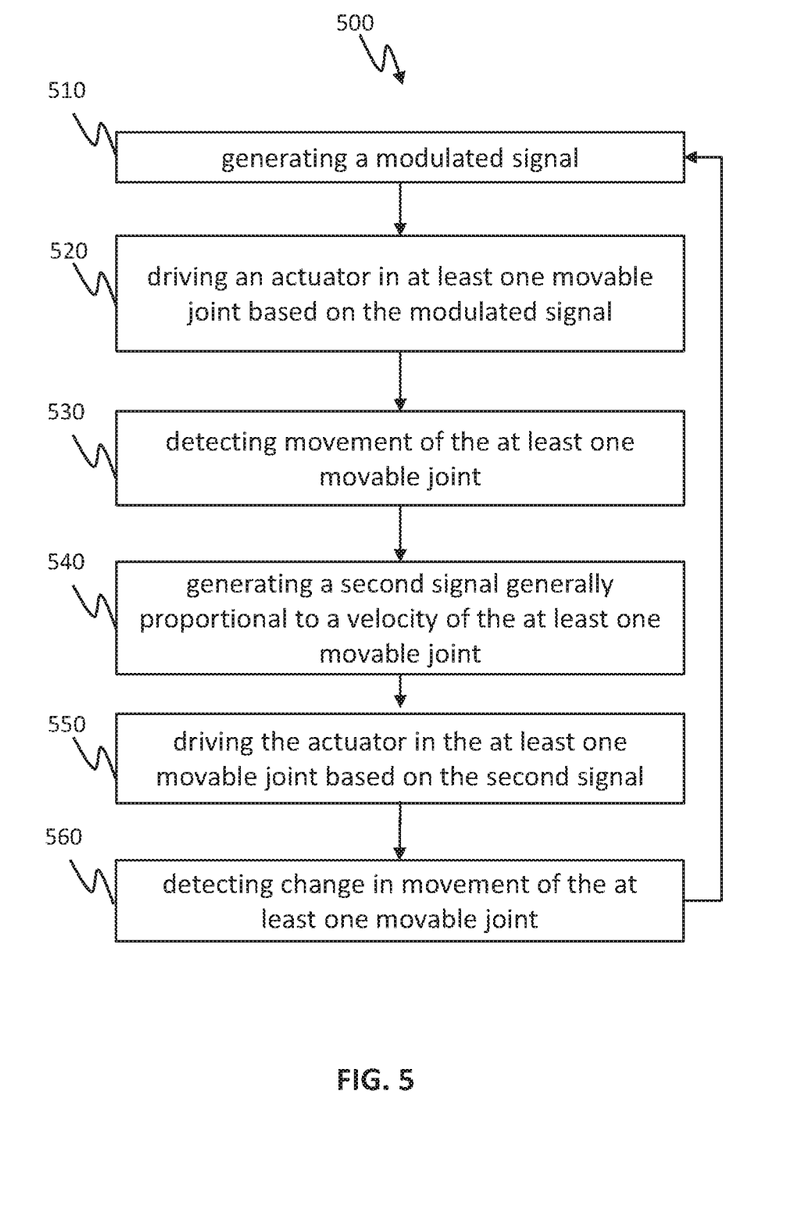
FIG. 5 is a flowchart of an exemplary variation of a method for assisting movement of a robotic arm with friction compensation.

For example, in some variations, as shown in FIG. 5, a method for assisting movement of a robotic arm may include generating a modulated signal 510, and driving an actuator in at least one movable joint in the robotic arm based on the modulated signal 520 to at least partially compensate for friction in the at least one movable joint, and detecting movement of the at least one movable joint 530. In some variations, the method may further include generating a second signal 540 generally proportional to a velocity of the at least one movable joint, driving the actuator in the at least one movable joint based on the second signal 550 (e.g., after movement of the joint commences). For example, the modulated signal and/or the second signal may correlate to command current for driving the actuator in the movable joint, such that the modulated signal and/or the second signal help compensate for friction forces resisting the movement of the robotic arm. The method may, for example, be implemented by a control system 300 described above with reference to FIG. 3. The control system 300 may simultaneously operate the robotic arm in gravity compensation mode and/or other suitable control modes.

Figure 6A:
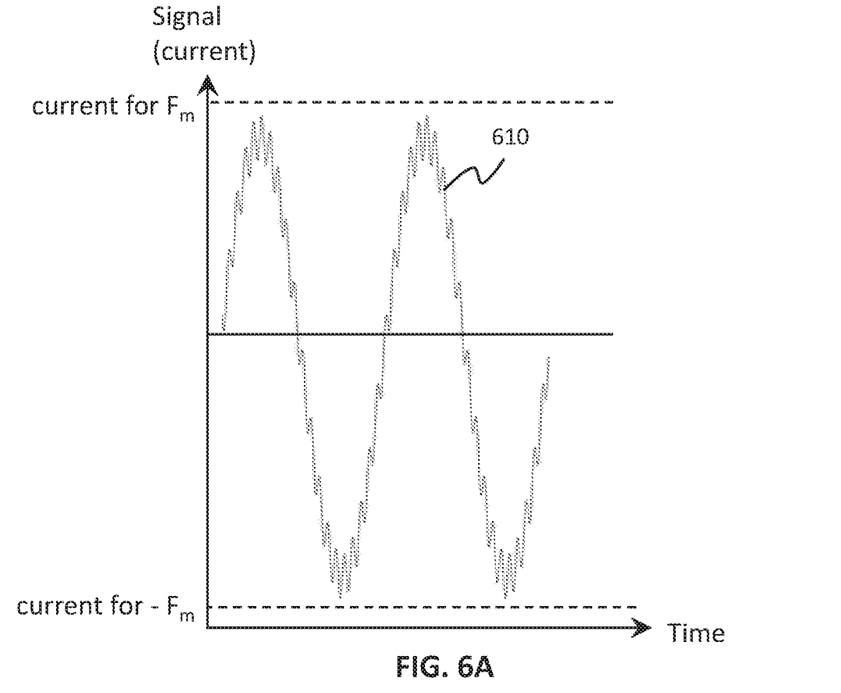
FIGS. 6A and 6B illustrate an exemplary modulated signal that may be used to control an actuator in a movable joint in the robotic arm when the joint is substantially not moving, in one variation of a friction compensation mode.

In some variations, generating a modulated signal 510 (e.g., via a processor and signal generator) and driving an actuator based on the modulated signal 520 may help provide compensation for static friction, in that the modulated signal may be used to drive an actuator for a movable joint while the movable joint is stationary (not moving). For example, FIG. 6A illustrates an exemplary modulated signal 610 that may be used to control an actuator in a movable joint in the robotic arm. The modulated signal 610 may be a multi-component dithering command signal, in that it may be described by at least two waveform components. For example, as suggested in the schematic of FIG. 6B, the modulated signal 610 may comprise or be defined by a first oscillating waveform 612 having a first frequency and being modulated by a second oscillating waveform 614 having a second frequency, where the second frequency is higher than the first frequency. For example, the first oscillating waveform 612 and/or the second oscillating waveform 614 may be a sine wave, though in other variations the first oscillating waveform 612 and/or second oscillating waveform 614 may be a square wave or other suitable oscillating waveform.

Figure 6B:
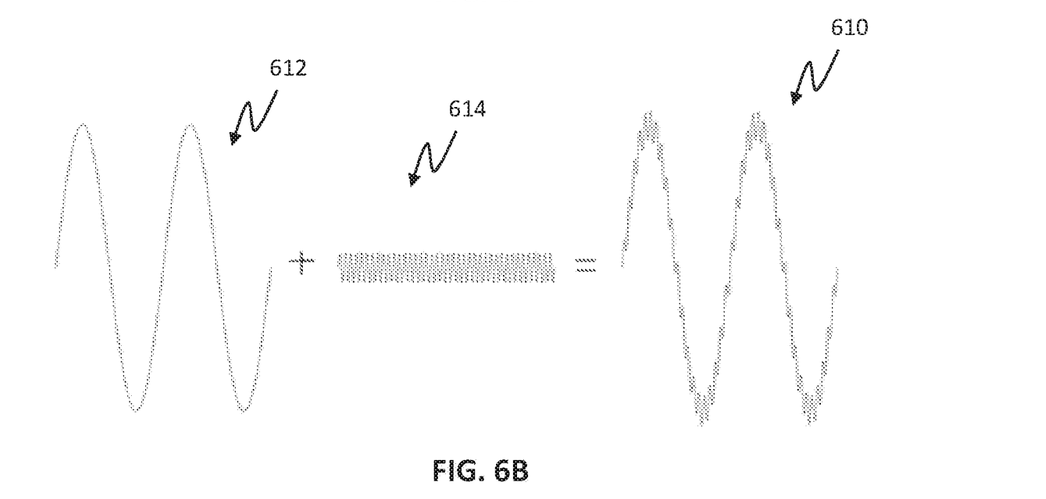

Generally, the modulated signal 610 including a low frequency waveform component and a high frequency waveform component may provide advantages or benefits not otherwise provided by either waveform component individually. For example, in at least some instances, when using a signal including only the low frequency waveform (e.g., similar to the waveform 612 shown in FIG. 6B) to drive an actuator for a movable joint in a friction compensation mode, it may still be difficult to successfully overcome static friction in the joint. The lower frequency waveform alone may decrease the responsiveness of friction compensation upon detection of an external force (e.g., user-applied force)

on the movable joint in the robotic arm. For example, an actuator driving a joint based on a lower frequency waveform will have fewer opportunities per second to successfully assist a user in moving the joint (compared to an actuator driving a joint based on a higher frequency waveform). Thus, driving an actuator for a movable joint with a low frequency signal may be unsuitable for friction compensation, as there may be a delay or sluggishness associated with any attempt to overcome static friction.

As another example, when using signals including only the higher frequency waveform (e.g., similar to the waveform 614 shown in FIG. 6B) to drive actuators for movable joints in a friction compensation mode, it may be difficult to overcome static friction and/or otherwise backdrive the actuator in any one particular joint of interest. This is at least in part because in this example, adjacent or nearby joints (which would also dithering in a similar manner as the joint of interest) are experiencing high acceleration, such that the adjacent or nearby joints are generating dynamic torque that is applied to the joint of interest, and vice versa. Thus, driving actuators for movable joints in a robotic arm with solely a high frequency signal may be unsuitable for friction compensation, as any attempt to overcome friction or backdrive a joint may be countered by the dynamic torques in the arm structure.

However, driving one or more actuators for at least one movable joint with a modulated signal 610 that includes both low frequency and the high frequency components, as described herein, may be advantageous. For example, such a modulated signal may provide responsiveness for friction compensation, without generating difficult-to-overcome dynamic torques. For example, the magnitude of the high frequency component may be low (because the high frequency component is modulated on top of the low frequency component, which may have a magnitude suitable for providing most of the friction compensation) and result in low acceleration and thus reduced dynamic effects among arm joints that are more controllable or manageable (and more easily overcome).

Generally, the frequency (or period), magnitude, offset, and/or other parameters or characteristics of the modulated signal may be individually tuned for one or more actuators in each joint module of a robotic arm. In some variations, such characteristics of the modulated signal may be determined based on, for example, static friction and/or dynamic friction within a joint (e.g., due to friction among moving components in an actuator, friction in a gear train coupled to output of an actuator, friction between arm links, etc.). A variety of factors such as weight (e.g., based on dimensions and/or material choice of robotic arm components), tightness of mechanical fit between moving components, degree of lubrication, and/or orientation of the joint (e.g., relative to gravitational force) of the joint, etc. may affect the amount of friction within a joint at any particular time.

For example, frequency of the slower (lower frequency) waveform component of the modulated signal may generally correspond to the responsiveness to detection of force (e.g., user-applied) on the movable joint in the robotic arm. As described above, in variations in which the slower component of the modulated signal has a lower frequency, there are fewer chances per second for the friction compensation force to be directed in the same direction as the user-applied force on the joint, and thus it may take a longer time for the friction compensation force to help a user overcome static friction when backdriving the joint. Conversely, in variations in which the slower component of the modulated signal has a higher frequency, there are more chances per second for the friction compensation force to be directed in the same direction as the user-applied force on the joint, and thus it may take less time for the friction compensation force to help a user overcome static friction when backdriving the joint. For example, if a user is attempting to manually rotate a particular movable joint in a first direction and the modulated signal 610 has a frequency of about 2 Hz, then there are about two times per second when the modulated signal is both at its maximum magnitude and corresponds to driving the actuator in the joint in the first direction. Thus, there are about two chances per second for the actuator (being driven based on the modulated signal 610) in that movable joint to assist the user in overcoming static friction. Particular values of frequency for the low frequency waveform component may be determined, for example, from usability and user studies. In some variations, the frequency of the slower waveform component of the modulated signal may be between about 0.5 Hz and about 5 Hz, between about 1 Hz and about 3 Hz, or about 2 Hz. For example, a low frequency waveform (e.g., sine wave) having a frequency of less than about 2 Hz may be sufficient to avoid causing user inconvenience.

As another example, frequency of the faster (higher frequency) waveform component of the modulated signal may generally correspond to enabling static friction to be overcome without moving the joint. For example, an actuator driven with a high frequency signal produces a high frequency torque, which may then overcome static friction without moving the joint. Additionally, the frequency of the faster waveform component may be selected to avoid generating audible noise (e.g., humming) and/or to avoid exciting one or more resonant frequencies in the robotic arm. For example, in some variations, the frequency of the faster waveform component may be less than or equal to about 200 Hz, less than or equal to about 150 Hz, less than or equal to about 125 Hz, or about 100 Hz. As another example, in some variations, the frequency of the faster waveform component may be between about 50 Hz and about 100 Hz to reduce or avoid audible noise.

As another example, magnitude or amplitude of the modulated signal (e.g., magnitude of the slower waveform component and/or the faster waveform component) may be selected or determined at least in part based on the static friction of the joint. For example, the modulated signal 610 may have a maximum magnitude that is generally the sum of the peak amplitudes of the slower waveform component and the faster waveform component where the peaks of the two waveform components coincide. Increasing the magnitude of the modulated signal (by increasing the magnitude of the slower waveform component and/or the increasing the magnitude of the faster waveform component) thus increases the magnitude of the actuator force that is available to help overcome the static friction of the movable joint. For example, the magnitude of the modulated signal may be such that the modulated signal is configured to drive the actuator in a movable joint with a force within the static friction band in both directions (e.g., $-F_m<$driving force resulting from signal$<F_m$). Accordingly, when the movable joint is being controlled by a modulated command current signal in friction compensation mode, the joint may be primed to nearly, but not quite, overcome friction in either actuator direction. As such, the modulated signal may provide partial friction compensation. An external force (such as that manually applied by a user) may, in combination with the active driving force provided based on the modulated signal, be sufficient to overcome static friction.

In some variations, the magnitude of the faster waveform component may be low relative to the magnitude of the slower waveform component. For example, the faster waveform component may have a magnitude that is a fraction of the magnitude of the slower waveform component. Generally, the magnitudes of the components of the modulated signal may be depend on particular characteristics of the hardware and application thereof, such as motor capability and arm joint dynamics. These magnitudes may, for example, be tuned experimentally.

In some variations, additionally or alternatively to modulation of the frequency of at least one component of the modulated signal, the magnitude or amplitude of the modulated signal may modulated. For example, the magnitude or amplitude of the slower, low frequency waveform component and/or the magnitude or amplitude of the faster, high frequency waveform component may vary over time (e.g., in response to varying static friction thresholds, etc.).

In some variations, the magnitude of the slower waveform component and/or faster waveform component of the modulated signal may be determined based on measurements of the static friction force $F_m$. The static friction force may be measured in one or more various suitable manners. For example, the static friction force may be measured during design and development processes and/or manufacturing. As another example, the static friction force may be measured during a calibration check (e.g., upon installation of the robotic system in an operating room, periodically after installation of the robotic system in an operating room, after use of the robotic arm for a predetermined number of performed surgical procedures, and/or before use of the robotic arm in every surgical procedure, etc.). For example, static friction of a joint may be determined by using a calibrated torque measurement device (e.g., a dynamometer, etc.) to backdrive the joint, where the empirically determined static friction force may be derived from the torque required (as measured by the torque measurement device) to make the joint begin moving.

As yet another example, the static friction force may be measured during a surgical procedure, which may allow for adjustment of the amplitude (and/or other suitable aspect) of the modulated signal during the procedure. For example, the amount of static friction may be measured by placing the arm in a gravity compensation mode (e.g., as described above) and slowly increase or decrease current to a joint-driving actuator until joint motion is detected. The amount of current required to move the joint may then be compared to known or predetermined backdrive parameters (e.g., determined during a previous check, etc.) to assess whether the amount of static friction has changed. One or more amplitude parameters may be automatically or manually (e.g., based on user input) adjusted in response to detecting a change in the amount of static friction in the joint. It should be understood that within a robotic arm having multiple movable joints, the static friction force for different movable joints may be measured at different times and accordingly, the signals used to perform friction compensation in different movable joints may be adjusted at different times. Furthermore, in a robotic surgical system including multiple robotic arms, the signals used to perform friction compensation in different robotic arms may be adjusted at different times.

Furthermore, in some variations, an offset of the modulated may be used to account for an unbalanced backdrive force that is required for a certain joint. For example, if the static friction in a joint is greater in a first direction than in a second direction different (e.g., opposite) from the first direction, then a greater magnitude signal may be required to help overcome or compensate for static friction for movement in the first direction than in the second direction. Accordingly, the modulated signal may include an offset such that it drives the actuator to have greater torque/force in the first direction than in the second direction. For example, such an offset in the modulated signal may be due to an offset in the slower, low frequency waveform component of the modulated signal. However, it should be understood that an offset may additionally or alternatively be due to an offset in the faster, high frequency waveform component of the modulated signal.

As shown in FIG. 5, the method may further include detecting movement of at least one movable joint 503 in the robotic arm. In some variations, movement of a joint in the robotic arm may be detected by one or more sensors in an actuator for the joint. For example, movement of a joint may be detected by an encoder configured to measure rotational position and/or velocity of an actuator in the joint, such as a change in rotational position or velocity of the actuator when the user begins to backdrive the movable joint in a particular direction. As another example, in variations in which a joint module includes a gear transmission (e.g., including an input coupled to a motor shaft and an output coupled to the moving portion of the joint), measured slop in the transmission, or measured rotational discrepancy or relative rotational changes between the input and the output of the transmission (e.g., via one or more encoders), may be used to determine movement of the joint. As yet another example (such as for a joint module including a gear transmission with high stiffness), any excessive motor current, or a measured motor current exceeding a predetermined threshold, may indicate movement of the joint.

In some variations, other sensors in the joint, such as suitable angle or proximity sensors in the joint module or arm structure itself, may additionally or alternatively be used to determine when the joint begins to move (e.g., due to the combination of user-applied force and friction compensation force provided by the modulated signal command current). Generally, movement of the joint may, for example, be identified when a change in rotational position exceeds a predetermined threshold (e.g., more than zero, or more than a predetermined number of degrees or radians) and/or when a change in velocity exceeds a predetermined threshold (e.g., more than zero, or more than a predetermined number of degrees or radians per second). As another example, movement of a joint may be detected by one or more force sensors, torque sensors, accelerometers, and/or other suitable sensors in or proximate the joint. As yet another example, movement of a joint (or a user's desire to move the joint) may be detected based on user contact with one or more arm links, such as with a touch or proximity sensor (e.g., capacitive sensor) located on an external surface of an arm link where the user would typically grasp the robotic arm when manipulating the arm.

The control system may additionally or alternatively monitor the velocity and/or position of the joint modules or arm links (e.g., with force or torque sensors, accelerometers, etc.) in order to determine the presence, magnitude, and direction of a user-applied force on one or more joint modules or arm links.

In some variations, the control system may incorporate one or more pre-defined parameters to help distinguish between movement that is accidental (e.g., a brief bump of a robotic arm) and a sudden intended shift in arm position. If an accidental movement is identified, then the control system may, in some variations, correct or reestablish arm position to compensate for the accidental movement (e.g., return the arm to the pose assumed just before the accidental movement occurred). For example, if duration of an external force on a joint (e.g., as measured by a force sensor or torque sensor in the joint module) is brief and is less than a predetermined threshold, then the control system may determine that the joint movement is accidental. In such an instance, the control system may continue to direct a modulated signal to the actuator in the joint module as if such accidental movement never occurred. Conversely, if duration of an external force on a joint is extended and is more than a predetermined threshold (e.g., at least 0.25 seconds, at least 0.5 seconds, or at least 1 second, etc.), then the control system may determine that the joint movement is intentional. In such instances, the control system may proceed to generate a second signal and drive the actuator based on the second signal as described below.

After detecting movement of at least one movable joint 530, the method may further include generating a second signal 540 (e.g., with a signal generator) and driving the actuator in the movable joint based on the second signal 550. In some variations, once the joint begins moving, the multi-component, modulated dithering signal described above may cease and be replaced by the second signal. The second signal may be different than the modulated dithering signal. In some variations, a second signal may be associated with at least partial compensation for friction after the joint in the robotic arm begins moving. Accordingly, the second signal may be used to drive the actuator in the moving joint and continue to assist the user as the user continues to move and manipulate the joint in the robotic arm.

Different variations of the second signal may be based on different friction models (e.g., Coulomb model, Coulomb and viscous model, Coulomb and viscous model with Stribeck effect as shown in FIG. 4, a simplified version of any of the preceding models, or any suitable friction model), in that the second signal may generate a force that generally tracks (but is less than) the modeled friction force opposing the movement of the joint. For example, in some variations, the second signal may be generally proportional to angular or rotational velocity of the movable joint. For example, in these variations, an actuator of a joint may be generally driven with a greater level of current to compensate for friction where the user moves the joint more quickly (or with less current where the user moves the joint more slowly). Furthermore, the direction of current (positive or negative) may change where the user changes the rotational direction of the joint.

Figure 7:
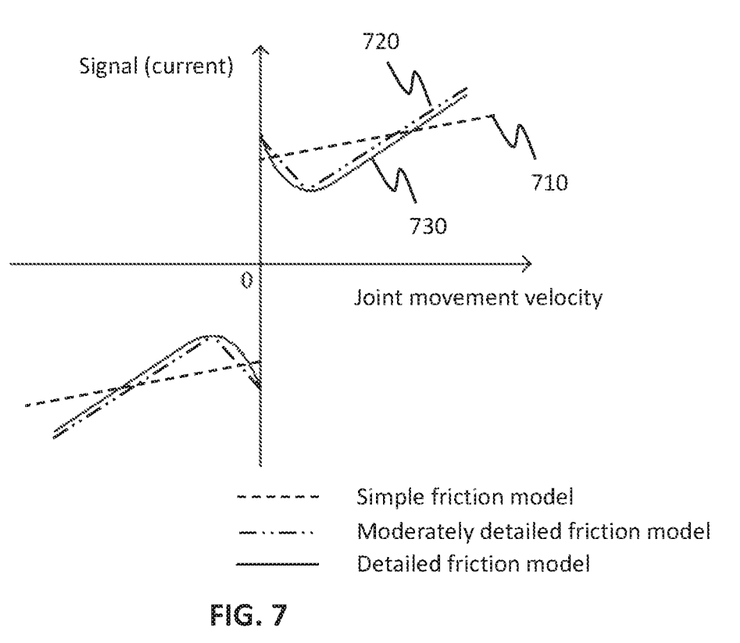
FIG. 7 illustrates exemplary variations of the second signal that may be used to control an actuator in a movable joint in the robotic arm, after the movable joint is determined to be moving.

FIG. 7 illustrates exemplary variations of the second signal that may be used to control an actuator in a movable joint in the robotic arm, after the movable joint is determined to be moving. For example, the second signal 710 may be based on a simplified friction model that is generally linearly proportional to velocity of the joint. As another example, as shown in FIG. 7, the second signal 720 may be based on a moderately detailed friction model that is generally linear and approximates a model for Coulomb friction and viscous friction model with Stribeck effect. As yet another example, as shown in FIG. 7, the second signal 730 may be based on an even more detailed friction model that is curvilinear and more closely approximates a model for Coulomb friction and viscous friction with Stribeck effect. In these and other suitable variations, the magnitude of the second signal relative to velocity (e.g., slope of the signal 710 as shown in FIG. 7) may, for example, be tuned based on measurements of dynamic friction force (e.g., during design and development processes, during manufacturing, during a calibration check, in real-time or near real-time, etc. similar to that described above for measurement of static friction force).

In some variations, the actuator in one or more movable joints may be driven to simultaneously compensate for both gravity and friction, by operating the robotic arm in both the gravity compensation mode and the friction compensation mode described above. For example, in some variations, the second signal may be generated to help compensate for imperfect gravity compensation, in addition to helping compensate for dynamic or viscous friction. For example, the friction model on which the second signal is based may be artificially tuned (e.g., in magnitude) to increase the overall applied load on the joint if the calculated force for gravity compensation is determined (e.g., with one or more sensors detecting additional backdriving due to gravitational force, etc.) to be insufficient for gravity compensation. Conversely, the friction model may be artificially tuned to decrease the overall applied load on the joint if the calculated force for the gravity compensation is determined to be excessive for gravity compensation. Furthermore, in some variations, an offset of the modulated signal described herein may be used to help overcome static friction (e.g., offset of the low frequency waveform component of the modulated signal) may additionally or alternatively be applied to help compensate for imperfect gravity compensation.

In some variations, as shown in FIG. 5, the method may further include detecting a change in movement of the at least one movable joint 560 of the robotic arm. In response to detecting a change in movement of the joint, the method may revert to generating a different kind of signal for driving the actuator of that joint. For example, upon detecting non-movement of the joint (e.g., when the user has stopped manipulating the joint of the robotic arm), the method may return to generating a modulated signal 510 and driving an actuator in the joint based on the modulated signal 520, which may again prepare the movable joint to be manipulated by the user in any direction with ease. Similar to that described above, when the control system returns to driving the actuator based on a modulated signal, the control system may simultaneously drive the actuator to help compensate for gravity. Accordingly, in some variations, the combination of gravity compensation and friction compensation may assist a user desiring to manually manipulate the robotic arm, leave the robotic arm temporarily, and continue manually manipulating the robotic arm with ease (and without complications caused by gravity and/or friction within the robotic arm).

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A method for assisting movement of a robotic surgical arm having at least one movable joint, the method comprising:
generating a first signal comprising a first oscillating waveform having a first frequency and being modulated by a second oscillating waveform having a second frequency, wherein the second frequency is higher than the first frequency; and
while a user is manually forcing the at least one moveable joint, driving an actuator in the at least one movable joint based on the first signal.

2. The method of claim 1, wherein the first oscillating waveform is a sine wave.

3. The method of claim 2, wherein the second oscillating waveform is a sine wave.

4. The method of claim 1 further comprising
while driving the actuator based on the first signal, driving the actuator to counteract gravity force enabling the robotic surgical arm to maintain a current pose by not drifting downward due to gravity.

5. A method for assisting movement of a robotic surgical arm having at least one movable joint, the method comprising:
detecting that a user is exerting manual force on the robotic surgical arm; and
in response to detecting that the user is exerting manual force on the robotic surgical arm, driving an actuator in the at least movable joint to assist the user in moving the arm, using a first signal that comprises a first oscillating waveform having a first frequency that is being modulated by a second oscillating waveform having a second frequency, wherein the second frequency is higher than the first frequency.

6. The method of claim 5, further comprising detecting movement of the at least one movable joint and in response driving the actuator in the at least one movable joint based on a previously presented second signal different from the first signal.

7. The method of claim 6, wherein amplitude of the second signal is generally linearly proportional to a velocity of the at least one movable joint.

8. The method of claim 6 wherein detecting that the user is exerting manual force and in response driving the actuator using the first signal occurs while the movable joint is stationary.

9. The method of claim 5 wherein the actuator assists the user in moving the arm whenever there is a peak in the first signal.

10. A robotic surgical system, comprising:
at least one robotic arm comprising at least one movable joint and an actuator configured to drive the at least one movable joint;
a controller configured to generate a modulated signal, the modulated signal comprising a first oscillating waveform having a first frequency and being modulated by a second oscillating waveform having a second frequency, wherein the second frequency is higher than the first frequency;
wherein the actuator is configured to drive the at least one movable joint, based on the modulated signal, in the same direction in which a user is exerting force on the movable joint.

11. The system of claim 10, wherein at least one of the first and second oscillating waveforms is a sine wave.

12. The system of claim 11, wherein the first frequency is between about 1 Hz and about 5 Hz.

13. The system of claim 12, wherein the second frequency is less than or equal to about 200 Hz.

14. The system of claim 10, wherein the controller configures the actuator to drive the at least one movable joint, based on the modulated signal, in response to detecting presence and direction of the user exerted force.

15. The system of claim 14 wherein the controller detects the user exerted force while the movable joint is stationary.

16. The system of claim 15, wherein the controller configures the actuator to drive the at least one movable joint based on a second signal different from the modulated signal, in response to having detected movement of the at least one movable joint while the actuator was driving the movable joint based on the modulated signal.

17. The system of claim 16, wherein the amplitude of the second signal is linearly proportional to a velocity of the at least one movable joint.

18. The system of claim 10, wherein the actuator is configured to drive the at least one movable joint to enable the robotic surgical arm to maintain a current pose by not drifting downward due to gravity.

19. The system of claim 10 wherein the actuator assists the user in moving the arm whenever there is a peak in the modulated signal.

* * * * *